US010722238B2

(12) United States Patent
Sutton et al.

(10) Patent No.: US 10,722,238 B2
(45) Date of Patent: *Jul. 28, 2020

(54) CLOT REMOVAL DEVICE FOR DEEP VEIN THROMBOSIS

(71) Applicant: Fusion Medical, Inc., Plymouth, MN (US)

(72) Inventors: Gregg Stuart Sutton, Maple Grove, MN (US); Eric Joseph Dille, Eden Prairie, MN (US); Jeffery Foster Larson, Dayton, MN (US)

(73) Assignee: Fusion Medical, Inc., Plymouth, MN (US)

( * ) Notice: Subject to any disclaimer, the term of this patent is extended or adjusted under 35 U.S.C. 154(b) by 193 days.

This patent is subject to a terminal disclaimer.

(21) Appl. No.: 15/850,694

(22) Filed: Dec. 21, 2017

(65) Prior Publication Data

US 2018/0110529 A1  Apr. 26, 2018

Related U.S. Application Data

(63) Continuation of application No. 13/890,892, filed on May 9, 2013, now Pat. No. 9,848,881.

(60) Provisional application No. 61/644,796, filed on May 9, 2012.

(51) Int. Cl.
| | | |
|---|---|---|
| *A61B 17/12* | (2006.01) | |
| *A61B 17/221* | (2006.01) | |
| *A61B 17/3207* | (2006.01) | |
| *A61B 17/22* | (2006.01) | |

(52) U.S. Cl.
CPC ...... *A61B 17/12109* (2013.01); *A61B 17/221* (2013.01); *A61B 17/320725* (2013.01); *A61B 17/320758* (2013.01); *A61B 17/12045* (2013.01); *A61B 2017/22054* (2013.01)

(58) Field of Classification Search
CPC ............ A61B 17/12109; A61B 17/221; A61B 17/3207; A61B 17/320725; A61B 17/320758; A61B 2017/22054; A61B 2017/320766; A61B 2017/320775
See application file for complete search history.

(56) References Cited

U.S. PATENT DOCUMENTS

| | | | |
|---|---|---|---|
| 5,250,060 A * | 10/1993 | Carbo | ............ A61B 17/320725 604/164.13 |
| 5,766,191 A | 6/1998 | Trerotola | |
| 5,843,103 A | 12/1998 | Laulfman | |
| 6,652,548 B2 | 11/2003 | Evans et al. | |

(Continued)

FOREIGN PATENT DOCUMENTS

| | | |
|---|---|---|
| WO | 200176458 | 10/2001 |
| WO | 2008006705 | 1/2008 |
| WO | 2014106847 | 7/2014 |

OTHER PUBLICATIONS

Office Action dated Dec. 19, 2018 for U.S. Appl. No. 15/008,253.

(Continued)

*Primary Examiner* — Ashley L Fishback
(74) *Attorney, Agent, or Firm* — Stoel Rives LLP

(57) ABSTRACT

The invention being disclosed describes a medical device for removal of a thrombus or clot in a vascular setting by using a rotational, expandable basket structure in combination with drug infusion, blood/particle aspiration and clot isolation by distal and proximal occlusion.

16 Claims, 3 Drawing Sheets

(56) References Cited

U.S. PATENT DOCUMENTS

| | | |
|---|---|---|
| 6,660,014 B2 | 12/2003 | Demarais et al. |
| 6,740,191 B2 | 5/2004 | Clarke et al. |
| 6,824,551 B2 | 11/2004 | Trerotola |
| 7,108,704 B2 | 9/2006 | Trerotola |
| 7,524,319 B2 | 4/2009 | Dubrul |
| 7,713,231 B2 | 5/2010 | Wulfman |
| 8,057,496 B2 | 11/2011 | Fischer |
| 2004/0220521 A1 | 11/2004 | Barbut |
| 2005/0124931 A1 | 6/2005 | Fulton et al. |
| 2008/0051873 A1 | 2/2008 | Cottone et al. |
| 2012/0143129 A1 | 6/2012 | Simpson et al. |
| 2014/0052103 A1 | 2/2014 | Cully et al. |
| 2014/0094841 A1 | 4/2014 | Sutton et al. |
| 2014/0371780 A1 | 12/2014 | Vale et al. |
| 2017/0020556 A1 | 1/2017 | Sutton et al. |

OTHER PUBLICATIONS

Office Action dated Nov. 27, 2017 for U.S. Appl. No. 15/008,253.
Office Action dated Mar. 2, 2017 for U.S. Appl. No. 13/890,892.
European Search Report dated Sep. 25, 2019 for EP17744980.8.

* cited by examiner

CLOT REMOVAL DEVICE FOR DEEP VEIN THROMBOSIS

RELATED APPLICATIONS

This application is a continuation of U.S. patent application Ser. No. 13/890,892, filed May 9, 2013, and titled "Clot Removal Device for Deep Vein Thrombosis," which claims the benefit of U.S. Provisional Application No. 61/644,796, filed May 9, 2012, both of which are hereby incorporated by reference in their entireties.

BACKGROUND OF THE INVENTION

The fields of interventional radiology and cardiology require the removal of clot in an artery or vein to reduce the possibility of embolisms and vascular occlusions. Particularly, in the case of deep vein thrombosis (DVT), a disease state in which a patient presents with a blood clot in a peripheral vein, the clot must be removed so that it does not embolize and cause a pulmonary artery occlusion which is usually fatal. These clots are typically removed with pharmacological or mechanical means. For instance urokinase, a lytic agent can be injected to the site of the clot to cause dissolution. Or mechanical removal is attempted with aspiration catheters or, alternatively catheter based baskets or other mechanical maceration means are employed.

The limitation of these devices include non-control of mobile clots during removal, systemic risks of lytic agents, and vein or arterial damage due to mechanical removal devices. Therefore, a need exists for an improved clot removal device for deep vein thrombosis

INVENTION DESCRIPTION

It is the purpose of this invention to describe an improved device for removing clot in an artery or vein. The device of this invention comprises a catheter based mechanism with a rotating basket structure in combination with aspiration means as well as distal and proximal clot isolation means.

The rotating basket structure comprises a metallic or polymeric struts in a spiral or straight configuration. The basket structure is, for example, expandable in diameter from catheter diameter (or less) to a much larger diameter, such as 10-20 mm. Diameter is typically independently controlled in a proximal handle mechanism. The diameter expansion control is independent of rotational speed. The rotational speed of the basket is controlled with the proximal handle means at speeds ranging from, for example 500-5000 rpm, and is driven by a DC motor integral to the handle means. The basket structure can be made of strut material that provides enough stiffness to macerate and emulsify clots but conformable enough to ride over and not damage venous or arterial structures such as valves.

Another embodiment of the basket structure provides 2 or 3 separate and independent basket structures that can be independently expanded or contracted.

Yet another embodiment of the invention provides a bi-modal basket shape which optimizes the function of the device when passed through venous or arterial valves.

The occlusive isolation element of the invention comprises distal and proximal occlusion elements that function by inflation or by mechanical expansion. The occlusion elements provide isolation of the clot during maceration and infusion/aspiration so as to inhibit particle embolization and maintenance of lytic concentrations.

The infusion/aspiration means element the invention comprises a distal to proximal lumen in the outer part of the catheter shaft. The lumen terminates within the occlusive isolation zone with an opening optimized for vacuum. The vacuum is provided proximally in the handle mechanism via a vacuum syringe or vacuum pump.

The above summary of the present invention is not intended to describe each discussed embodiment of the present invention. This is the purpose of the figures and the detailed description that follows.

DRAWINGS

The invention may be more completely understood in connection with the following drawings, in which.

Figure 1:
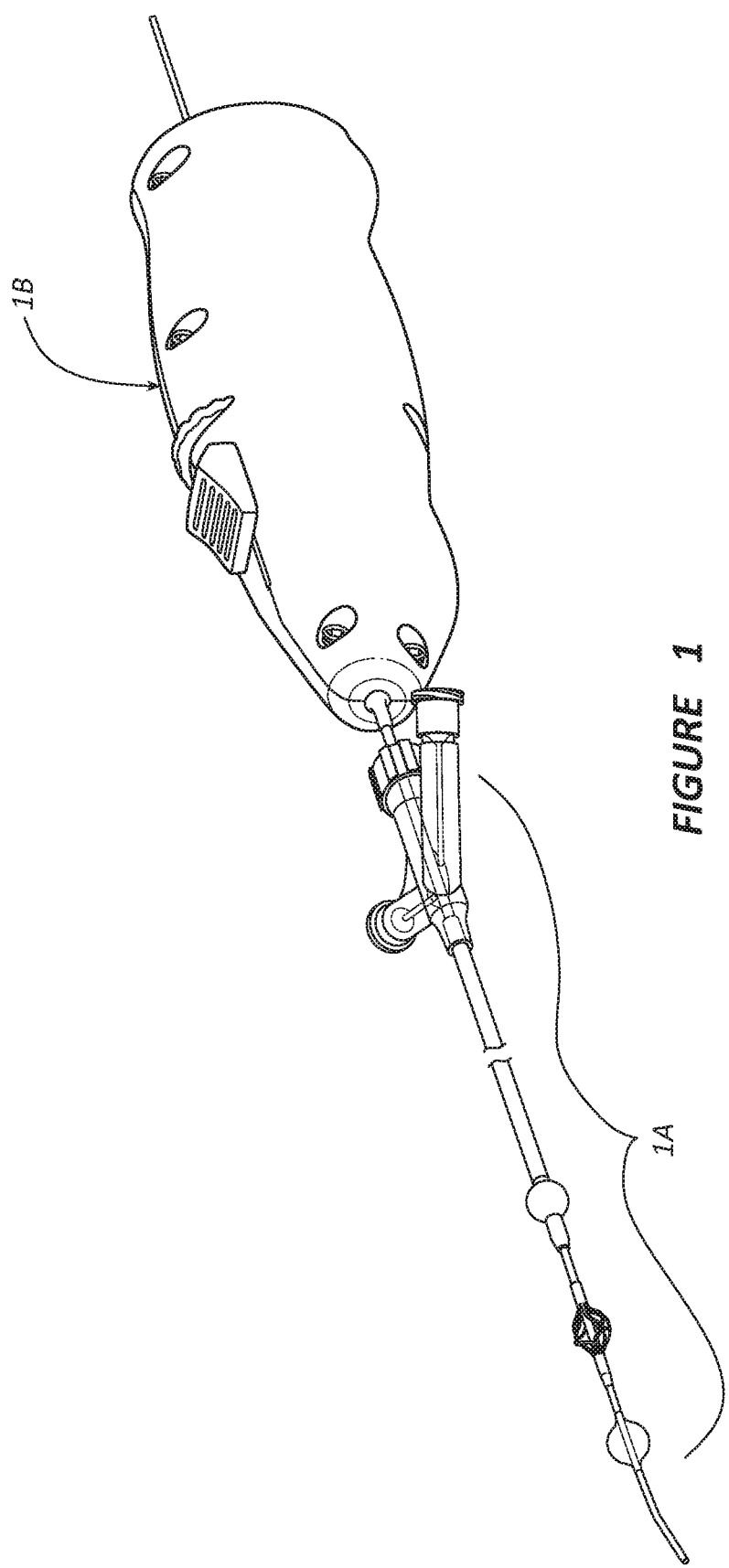
FIG. 1 shows the device in it's entirely from delivery/catheter portion (1A) to proximal control handle (1B).
Figure 2:
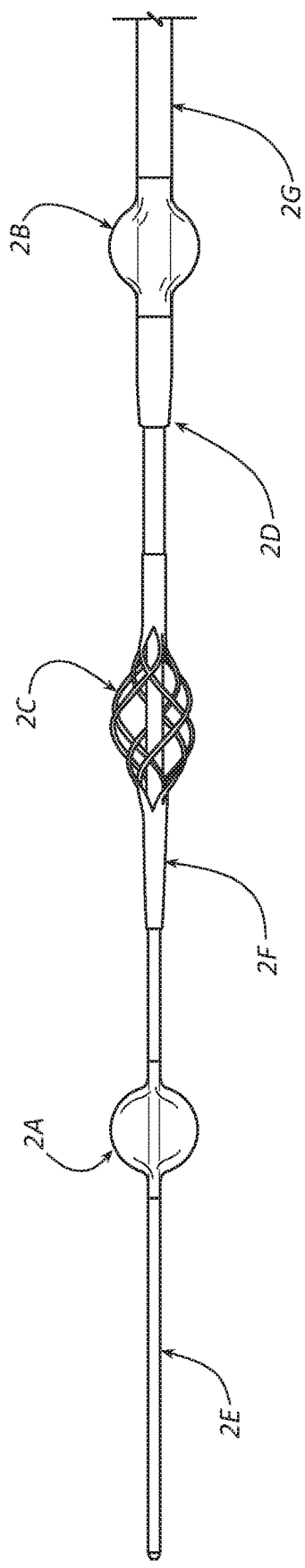
FIG. 2 shows the working end, or distal end of the device. Elements 2A and 2B are the occlusive balloon means. 2C shows the basket in the mid-expansion state. 2D is the infusion/aspiration port. 2E is the guidewire member portion of the device, 2F is the rotational member of the device and 2G is the infusion/aspiration outer sheath member of the device.
Figure 2A:
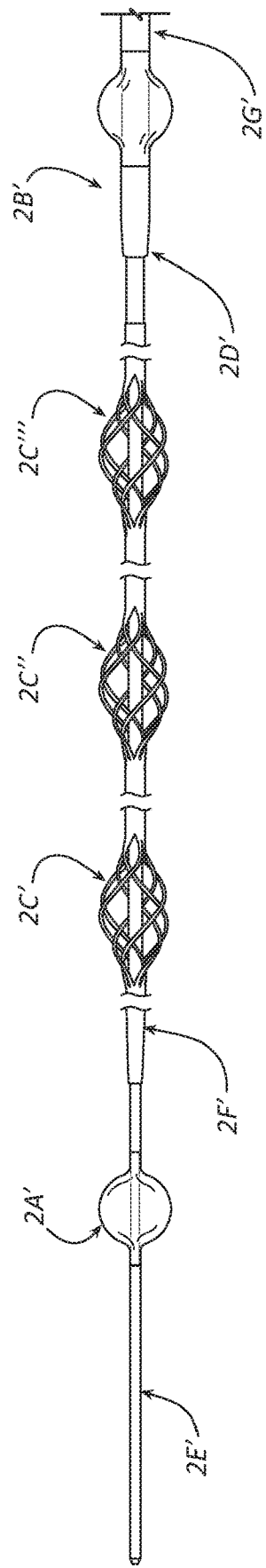

FIG. 2A shows the working end, or distal end of another embodiment of the device. Elements 2A' and 2B' are the occlusive balloon means. A first basket 2C', a second basket 2C", and a third basket 2C''' are each shown in the mid-expansion state. 2D' is the infusion/aspiration port. 2E' is the guidewire member portion of the device, 2F' is the rotational member of the device and 2G' is the infusion/aspiration outer sheath member of the device.

Figure 3:
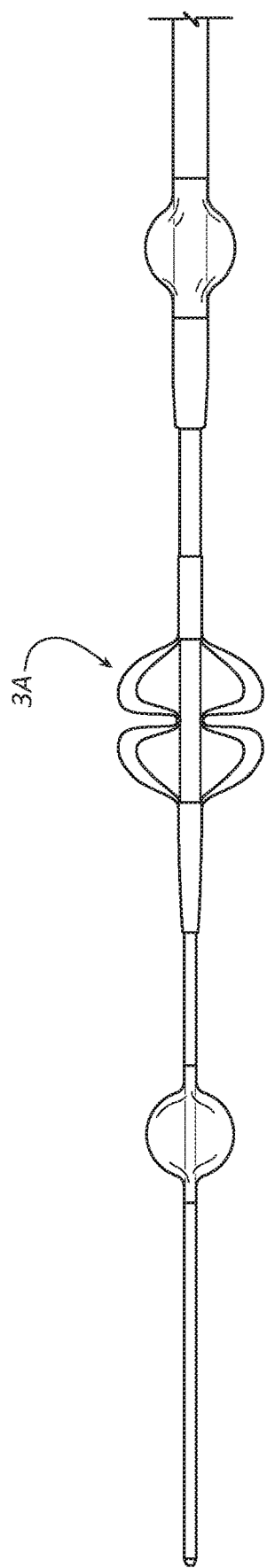

FIG. 3 shows another embodiment of the device which exhibits an axially bi-modal basket design (3A).

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

The present invention is directed to a medical device for removing thrombus or clot from the vasculature comprising, in an example embodiment, a distal occlusive element mounted on an inner guidewire member. A catheter member may be slideable over the guidewire member that has a distal clot macerating basket structure that is diametrally expandable. A basket structure can contain a plurality of struts to form an expanded elliptical shape or bi-modal elliptical shape. The catheter member and basket are rotatable at (500-10,000) rpm and controlled at a proximal handle member.

In some implementations the devices includes an outer infusion/aspiration catheter sheath that is slideable over the rotational catheter member and contains a proximal occlusion member and is operably connected to the proximal control handle. A proximal control handle that provides rotational speed control, basket expansion/contraction and infusion/aspiration fluid inputs may be included. The proximal control handle comprising an internal DC motor, gearing/belt system and through lumen access. The thrombus or clot removing device can be arranged such that occlusive isolation, basket rotation (clot maceration) and infusion/aspiration are operating simultaneously or in combination.

While the present invention has been described with reference to several particular implementations, those skilled in the art will recognize that many changes may be made hereto without departing from the spirit and scope of the present invention.

I claim:

1. A catheter for blockage removal for a circulatory system, comprising:
    a main tubular shaft;
    an isolation element coupled to the main tubular shaft, the isolation element includes a first expandable isolation member and a second expandable isolation member;
    a first rotational macerating element coupled to the main tubular shaft, the first rotational macerating element disposed between the first expandable isolation member and the second expandable isolation member; and
    a second rotational macerating element coupled to the main tubular shaft, the second rotational macerating element disposed between the first expandable isolation member and the second expandable isolation member and distal to the first rotational macerating element,
    wherein the first and second rotational macerating elements are expandable.

2. The catheter of claim 1, further comprising a third rotational macerating element coupled to the main tubular shaft, the third rotational macerating element disposed between the first expandable isolation member and the second expandable isolation member and distal to the first and second rotational macerating elements.

3. The catheter of claim 1, further comprising an aspiration port disposed between the first expandable isolation member and the second expandable isolation member.

4. The catheter of claim 3, wherein the aspiration port is distal to the first expandable isolation member and proximal to the first rotational macerating element.

5. The catheter of claim 1, wherein the first and second rotational macerating elements include at least two struts.

6. The catheter of claim 1, wherein the first and second rotational macerating elements are expandable independent of each other.

7. The catheter of claim 1, wherein the first and second rotational macerating elements have a basket structure.

8. The catheter of claim 7, wherein the basket structure of the first and second rotational macerating elements is elliptical when expanded.

9. The catheter of claim 1, wherein the first and second expandable isolation members are inflatable.

10. The catheter of claim 1, wherein at least one of the first and second rotational macerating elements has a bi-modal shape.

11. A catheter for blockage removal for a circulatory system, comprising:
    a main tubular shaft;
    an isolation element coupled to the main tubular shaft, the isolation element includes a first expandable isolation member and a second expandable isolation member;
    a first expandable rotational macerating element coupled to the main tubular shaft, the first expandable rotational macerating element disposed between the first expandable isolation member and the second expandable isolation member; and
    a second expandable rotational macerating element coupled to the main tubular shaft,
    wherein the first and second expandable rotational macerating elements are expandable independent of each other.

12. The catheter of claim 11, wherein the second expandable rotational macerating element is disposed between the first expandable isolation member and the second expandable isolation member and distal to the first rotational macerating element.

13. The catheter of claim 11, wherein the first and second rotational macerating elements include at least two struts that overlap each other.

14. The catheter of claim 11, further comprising a third expandable rotational macerating element coupled to the main tubular shaft, the third expandable rotational macerating element disposed between the first expandable isolation member and the second expandable isolation member and distal to the first and second rotational macerating elements.

15. The catheter of claim 11, further comprising an aspiration port disposed between the first expandable isolation member and the second expandable isolation member.

16. The catheter of claim 15, wherein the aspiration port is distal the first expandable isolation member and proximal to the first rotational macerating element.

* * * * *